(12) United States Patent
Park et al.

(10) Patent No.: US 10,441,616 B2
(45) Date of Patent: Oct. 15, 2019

(54) PHARMACEUTICAL COMPOSITION FOR TREATING OR PREVENTING SENSORINEURAL HEARING LOSS, CONTAINING CYSTEINYL LEUKOTRIENE RECEPTOR ANTAGONIST AND GINKGO LEAF EXTRACT

(71) Applicant: AJOU UNIVERSITY INDUSTRY-ACADEMIC COOPERATION FOUNDATION, Suwon-si, Gyeonggi-do (KR)

(72) Inventors: Sang Myun Park, Suwon-si (KR); Jung Sub Park, Suwon-si (KR); Yun Hoon Choung, Suwon-si (KR); Yeon Ju Kim, Suwon-si (KR)

(73) Assignee: AJOU UNIVERSITY INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 363 days.

(21) Appl. No.: 15/120,580

(22) PCT Filed: Feb. 23, 2015

(86) PCT No.: PCT/KR2015/001693
§ 371 (c)(1),
(2) Date: Jan. 9, 2017

(87) PCT Pub. No.: WO2015/126192
PCT Pub. Date: Aug. 27, 2015

(65) Prior Publication Data
US 2017/0165309 A1 Jun. 15, 2017

(30) Foreign Application Priority Data

Feb. 20, 2014 (KR) ........................ 10-2014-0019665

(51) Int. Cl.
A61K 36/16 (2006.01)
A61K 31/47 (2006.01)
A61K 31/573 (2006.01)

(52) U.S. Cl.
CPC .............. *A61K 36/16* (2013.01); *A61K 31/47* (2013.01); *A61K 31/573* (2013.01); *A61K 2121/00* (2013.01); *A61K 2300/00* (2013.01)

(58) Field of Classification Search
CPC .. A61K 2300/00; A61K 31/47; A61K 31/573; A61K 36/16; A61K 2121/00
See application file for complete search history.

(56) References Cited

U.S. PATENT DOCUMENTS

| 5,897,864 A * | 4/1999 | Cohen ................... A61K 36/16 424/752 |
| 2007/0249695 A1* | 10/2007 | Kawata .............. A61K 31/4035 514/382 |
| 2009/0306225 A1* | 12/2009 | Lichter ................ A61K 9/0046 514/772.1 |

FOREIGN PATENT DOCUMENTS

KR 1020070028462 KR 12/2007

OTHER PUBLICATIONS

Ertugay CK, Cingi C, Yaz A, San T, Ulusoy S, Erdogmus N, Ertugay OC, "Effect of combination of montelukast and levocetirizine on otitis media with effusion: a prospective, placebo-controlled trial" Acta OtoLaryngologica, (2013)133:12,1266-1272;doi:10.3109/0001648 (Year: 2013).*

Christopher Hobbs, Ginkgo, Elixir of Youth:modern medicine from an ancient tree, Botanica Press, (Capitola,CA..), 1991.ISBN-13:978-0961847036 (Year: 1991).*

Burschka et al., "Effect of treatment with Ginkgo Biloba extract EGb 761 (oral) on unilateral idiopathic sudden hearing loss in a prospective randomized double-blind study of 106 outpatients", Eur Arch Otorhinolaryngol (2001) 258: 213-219.

Kumar et al., "Role of Gingkgo Biloba Extract in Acquired Sensorineural Hearing Loss", Indian Journal of Otolaryngology and Head and Neck Surgery, vol. 52 No. 3, Jul.-Sep. 2000.

Yang et al., "EGb 761 (Gingko biloba) protects cochlear hair cells against ototoxicity induced by gentamicin via reducing reactive oxygen species and nitric oxide-related apoptosis", Journal of Nutritional Biochemistry 22 (2011) 886-894.

* cited by examiner

*Primary Examiner* — Aaron J Kosar
(74) *Attorney, Agent, or Firm* — Workman Nydegger

(57) ABSTRACT

The present invention provides a compound having an effect of preventing and/or treating the damage or degeneration of cochlear (and vestibular) mother cells and spiral ganglion neurons by downregulating a cysteinyl leukotriene receptor. Particularly, the present invention provides a composition for preventing or treating sensorineural hearing loss, containing a cysteinyl leukotriene receptor and a *Ginkgo biloba* extract as active ingredients, on the basis of the co-administration of a cysteinyl leukotriene receptor and a *Ginkgo biloba* extract having an excellent effect of protecting hearing.

20 Claims, 10 Drawing Sheets

[Fig. 1]
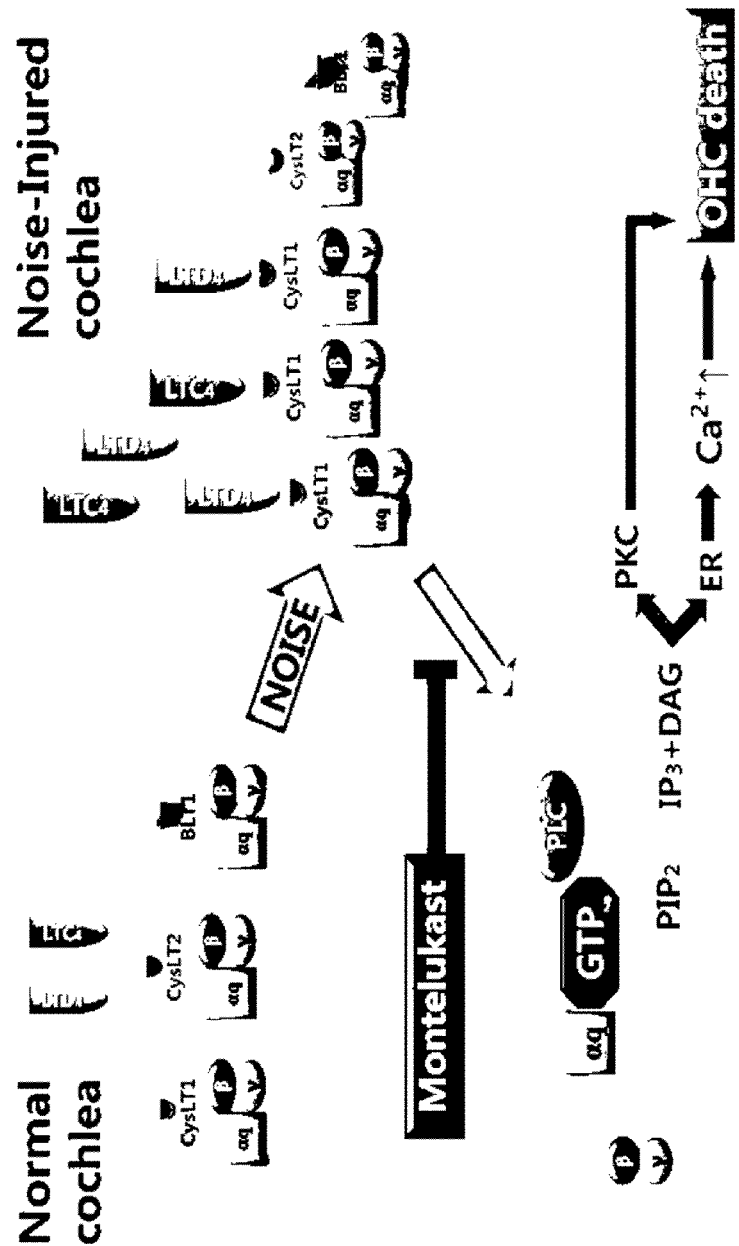

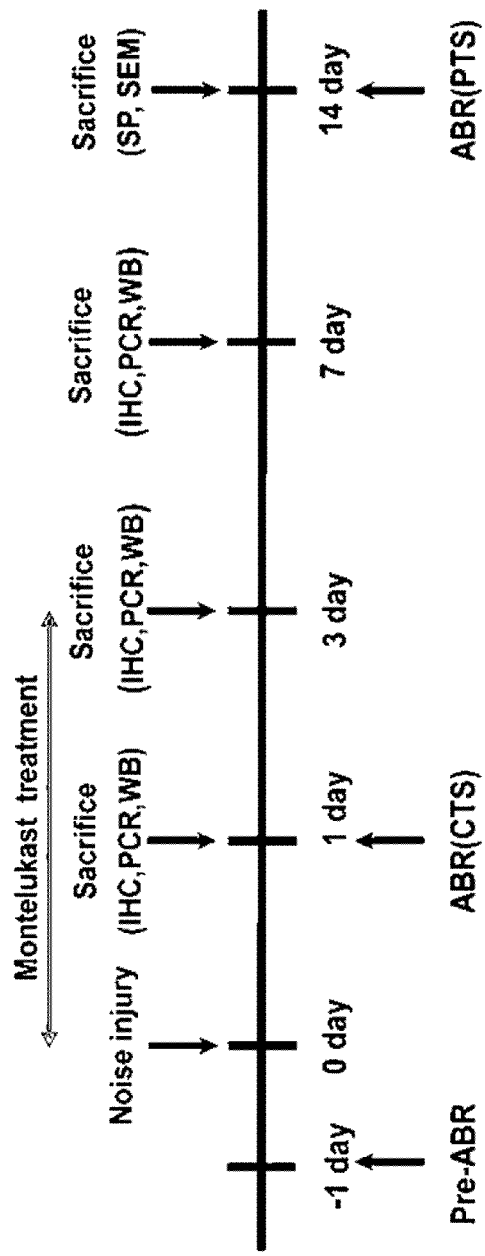
[Fig. 2]

[Fig. 3]
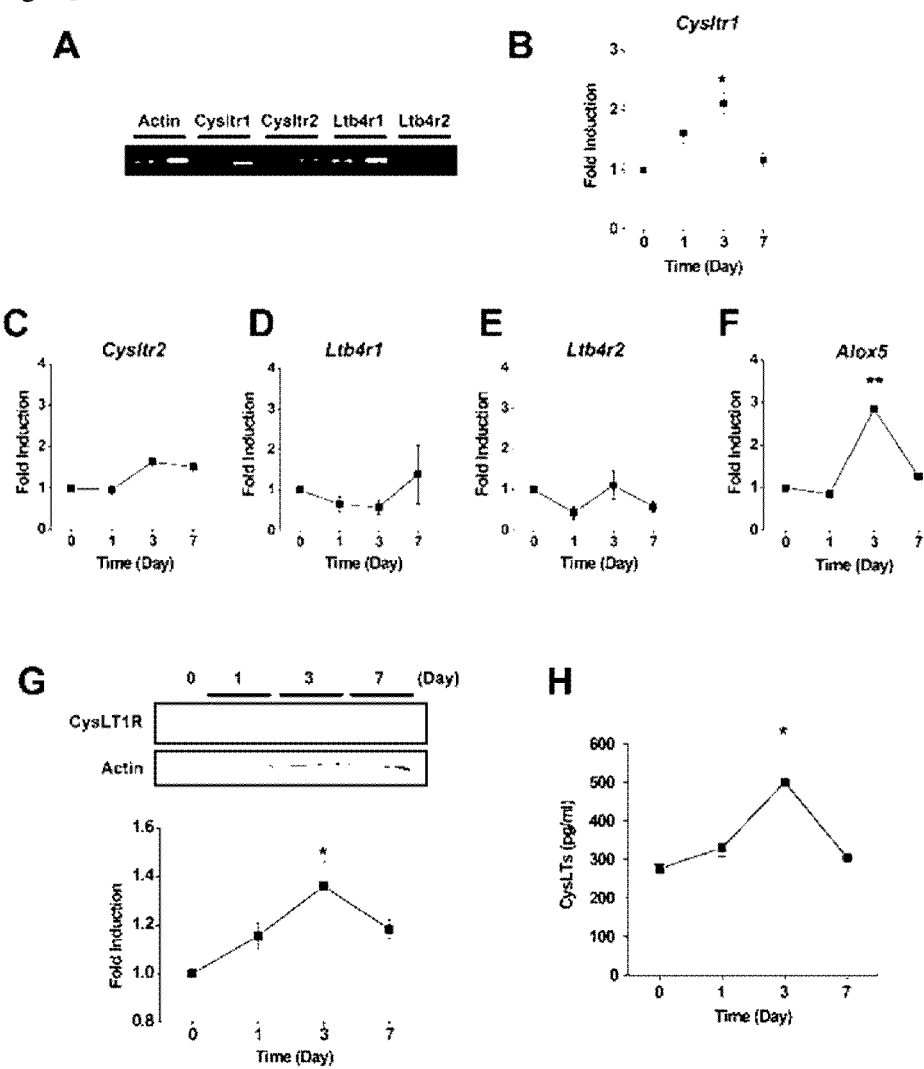

[Fig. 4]
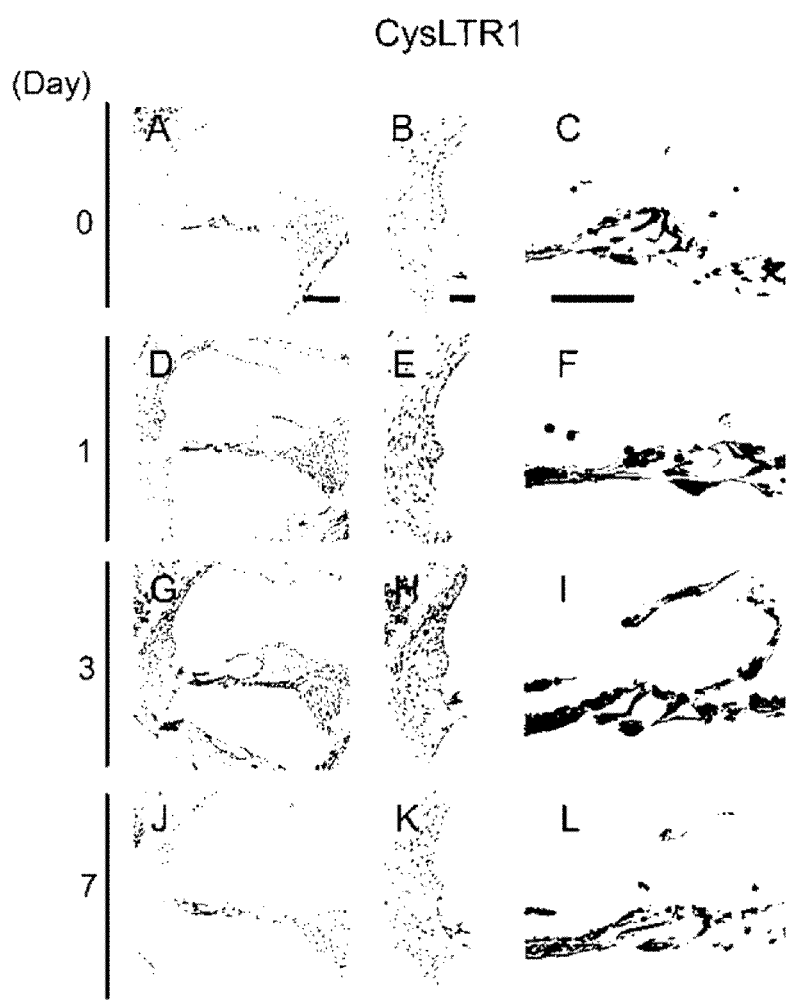

[Fig. 5]
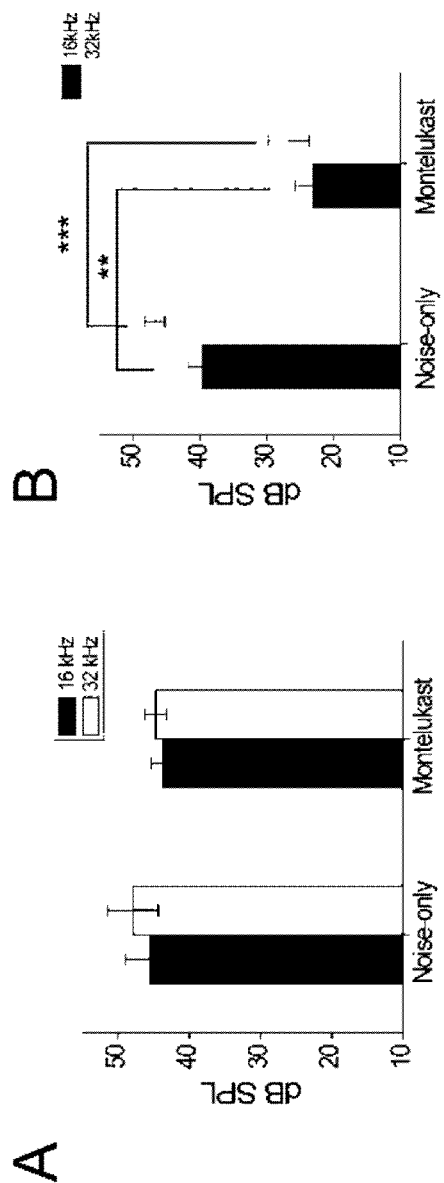

[Fig. 6]
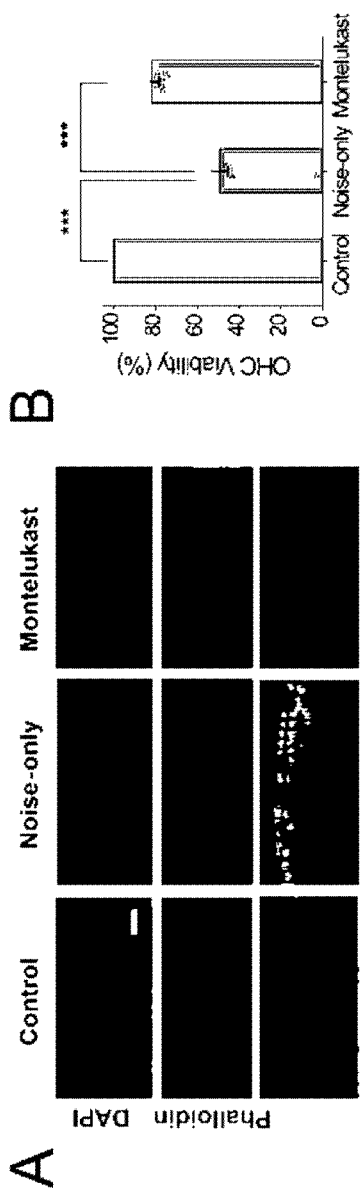

[Fig. 7]

[Fig. 8]
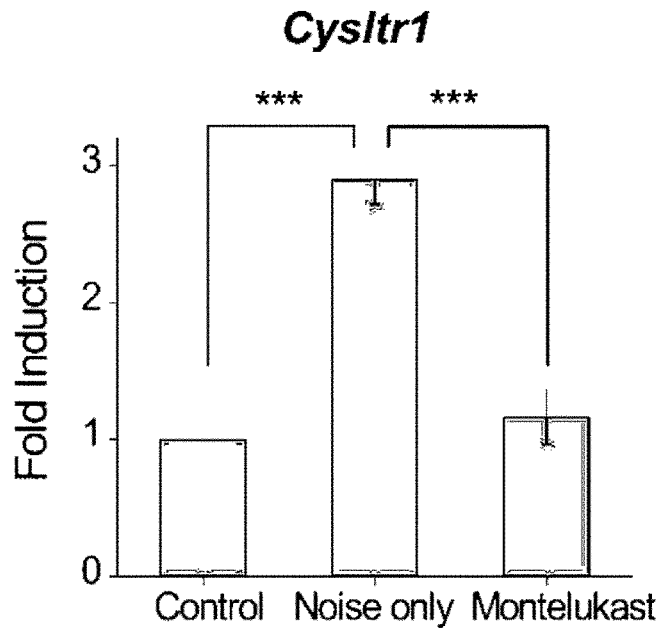
[Fig. 9]
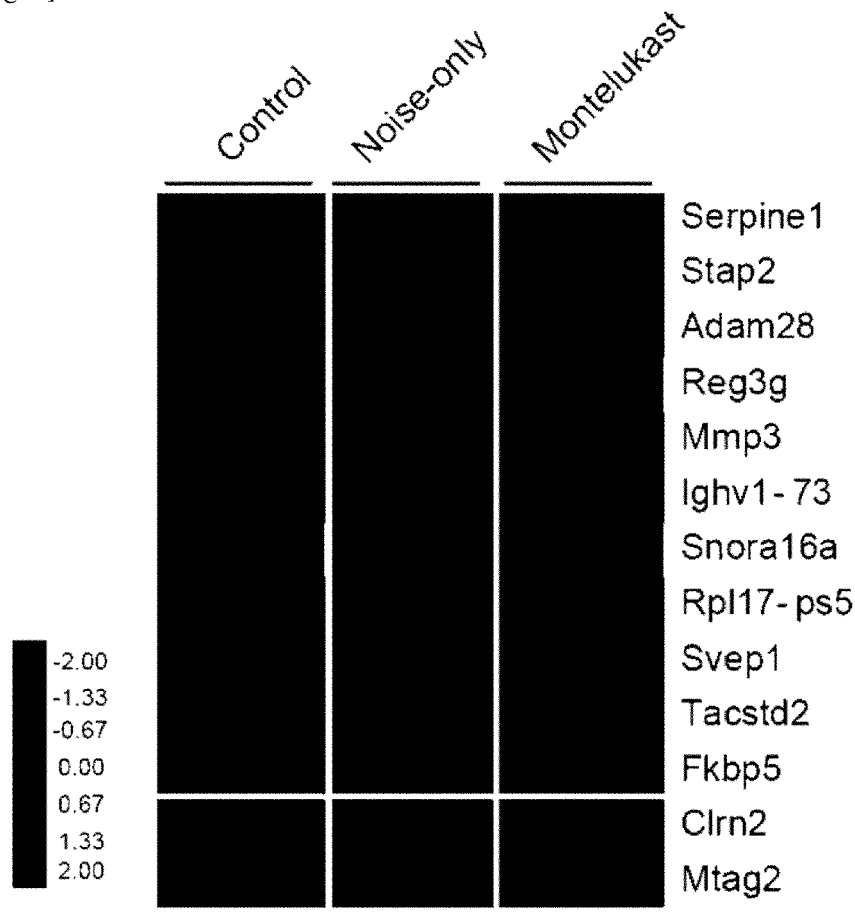

[Fig. 10]
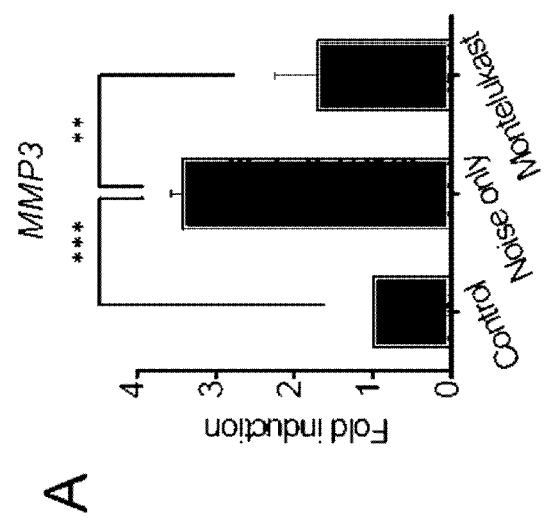
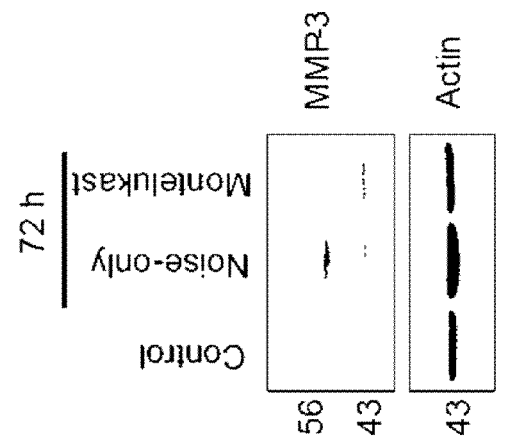

[Fig. 11]
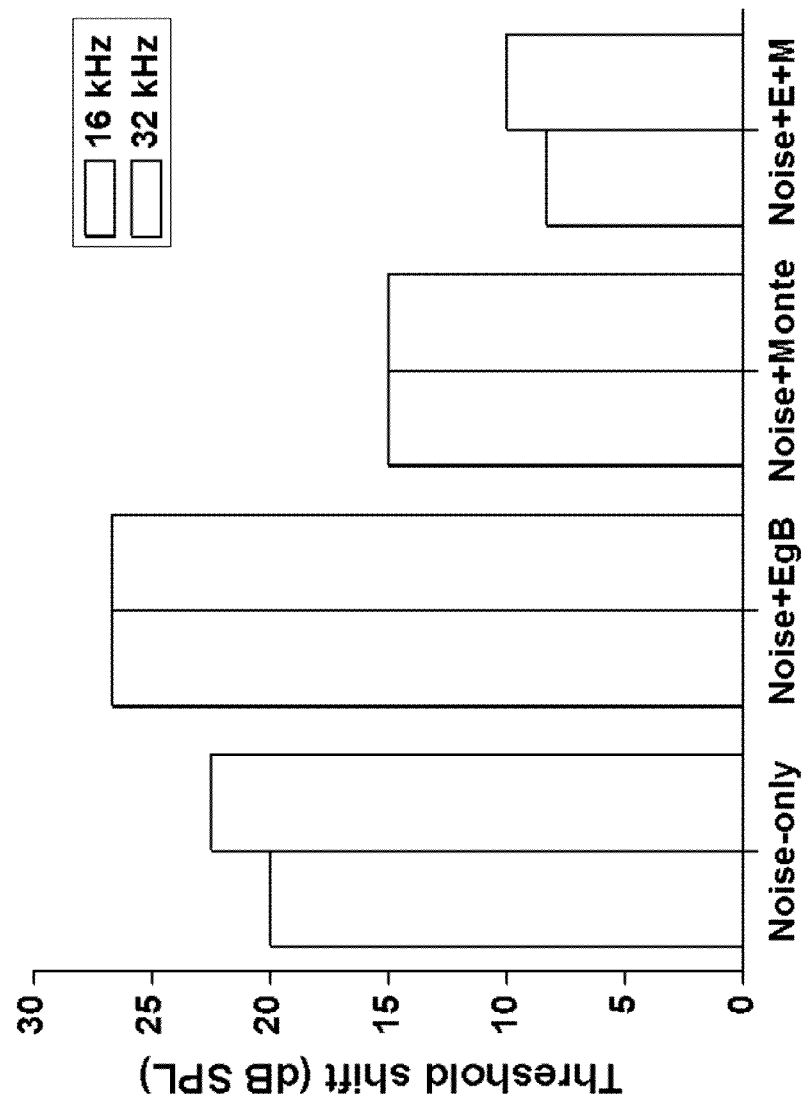

PHARMACEUTICAL COMPOSITION FOR TREATING OR PREVENTING SENSORINEURAL HEARING LOSS, CONTAINING CYSTEINYL LEUKOTRIENE RECEPTOR ANTAGONIST AND GINKGO LEAF EXTRACT

TECHNICAL FIELD

The present invention relates to a pharmaceutical composition for treating or preventing sensorineural hearing loss, in which the pharmaceutical composition includes a cysteinyl leukotriene receptor antagonist and a *Ginkgo biloba* extract.

BACKGROUND ART

Sensorineural hearing loss is directly related with quality of life, and thus, become a health-related issue which is rapidly emerging in worldwide. Approximately 5% of the world population is troubled with hearing loss caused by noise exposure with high intensity, and as lifespan is increased, occurrence of the sensorineural hearing loss depending on aging has been on the rise every year. Noise-induced hearing loss (NIHL) is one of the most common occupational diseases in advanced countries and developing countries. A lot of researches for preventing and treating the NIHL have been conducted by understanding pathophysiological mechanisms of apoptosis in the cochlea due to noise.

According to those proposed in many of accumulated researches, a representative cause of main causes in the occurrence of the sensorineural hearing loss is apoptosis of hair cells caused by an inflammatory response generated in the cochlea as a hearing organ. The inflammatory response in the cochlea is a response in which fiber cells present in the spiral ligament of the cochlea, support cells of Corti's organ, or immune cells such as macrophages and leukocytes in the blood act to the damaged sites to remove antigens or remove damaged tissues, thereby helping recovery of a normal state, when the damage to constituted tissues is generated by penetration of external substances such as virus or bacteria or strong pressure such as noise. Acute inflammation may be cured in a short period, but in any case, when infection or damage is continuously maintained, the immune cells are continuously left. Accordingly, mediators such as chemokines and cytokines are secreted to damage the surrounding tissues and cause chronic inflammatory diseases such as Allergy, autoimmune, and pancreatitis. The inflammatory response mediators are substances that promote the inflammatory response while the inflammatory response starts and proceeds. The inflammatory response mediators are generated in neutrophils, immune cells such as macrophages, and platelets and include chemokines, cytokines, fat-soluble mediators, and the like. Eicosanoid is a fat-soluble mediator originated from the cell membrane to promote the inflammatory response. The eicosanoid is synthesized from arachidonic acid, a cyclooxygenase (COX) pathway generates many prostaglandins (PGs) and thromboxanes (TXs), and a lipoxygenase (LOX) pathway generates leukotrienes (LTs) and lipoxins (LXs). The LTs are divided into cysteinyl leukotrienes (CysLTs; LTC4, LTD4, and LTE4) and LTB4, CysLTs are known as a representative cause of allergic rhinitis and asthma, and found to be involved to the occurrence of neurodegenerative disorders and cardiovascular diseases according to a recent report. However, all the eicosanoid do not cause or continue the inflammatory diseases, and in the case of PGD2 or 15d-PGJ2, anti-inflammatory effects are reported a lot. Thus, possibility that blocking of a lower pathway based on characteristics for each disease or for each tissue is successful as an effective treatment method is higher than broad inhibition of generation of the eicosanoid.

In the case of existing noise exposure, wearing of hearing protection devices (HPD) is a unique prevention method, but the wearing in the actual industrial sites is limited due to the disadvantages that communication between operators is blocked under a noisy environment. Accordingly, many researchers conduct continuous researches for the discovery of orally administrated drugs for treating and preventing hearing loss in order to overcome these limitations, but orally administrated drugs having clear effects on noise-induced hearing loss or presbycusis are not developed.

DISCLOSURE

Technical Problem

The present invention is directed to develop and discover a new treating drug of sensorineural hearing loss in which prevention and treatment by a drug are not established until now, and provides a new use of montelukast capable of suppressing the progression of hearing loss by downregulating a cysteinyl leukotriene receptor. Further, the present invention is also directed to provide a new use of co-administration on the basis of an excellent effect of improving hearing loss, when treating a *Ginkgo biloba* extract together with the cysteinyl leukotriene receptor antagonist.

Technical Solution

The present invention is directed to provide a compound having an effect of preventing and/or treating the damage or degeneration of cochlear (and vestibular) mother cells and spiral ganglion neurons by downregulating a cysteinyl leukotriene receptor. Particularly, the compound according to the present invention may be provided as a composition for preventing or treating sensorineural hearing loss.

In addition, the present invention provides a composition for preventing or treating sensorineural hearing loss, in which the composition includes the cysteinyl leukotriene receptor and a *Ginkgo biloba* extract as active ingredients.

One aspect of the present invention provides a pharmaceutical composition for preventing or treating sensorineural hearing loss, in which the pharmaceutical composition includes a compound represented by the following Chemical Formula 1 as an active ingredient.

[Chemical Formula 1]

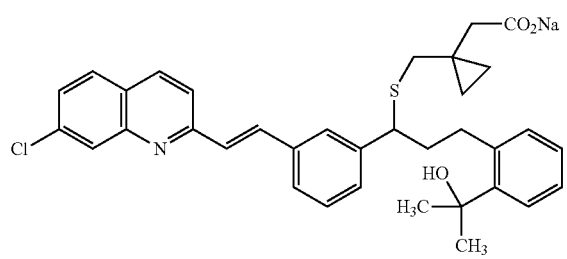

The compound represented by Chemical Formula 1 acts as an antagonist of a cysteinyl leukotriene receptor. Particularly, among cysteinyl leukotriene receptors, the antagonist is an antagonist of a Type 1 receptor.

The pharmaceutical composition may be administrated as noise injury posttreatment and continuously administrated in the amount of 0.8 to 10 mg/kg for 4 to 14 days.

The compound represented by Chemical Formula 1 may reduce the expression of a matrix metalloproteinase-3 (Mmp3) gene.

The compound represented by Chemical Formula 1 may reduce the level of zinc-dependent endopeptidase.

Further, the compound represented by Chemical Formula 1 may be co-administrated with a drug such as prednisolone and methylprednisolone.

Advantageous Effects

According to the present invention, it is possible to provide a pharmaceutical composition for effectively preventing and/or treating sensorineural hearing loss.

DESCRIPTION OF DRAWINGS

FIG. 1 is a schematic diagram illustrating a pharmacological mechanism of montelukast of Chemical Formula 1.

FIG. 2 is a chart illustrating an experimental schedule according to an exemplary embodiment of the present invention.

FIG. 3 is a photograph and a graph observing an effect of increasing only a CysLT1 receptor by noise exposure.

FIG. 4 is a photograph observing a portion where only the CysLT1 receptor is increased by noise exposure.

FIG. 5 is a graph observing a change in hearing threshold through an auditory brainstem response test.

FIG. 6 is a photograph A and a graph B confirming an effect of decreasing apoptosis of montelukast using a fluorescent marker.

FIG. 7 is a photograph confirming an effect of decreasing apoptosis of the montelukast using a scanning electron microscope.

FIG. 8 is a graph confirming an effect of decreasing expression of the CysLT1 receptor of the montelukast using a polymerase chain reaction (PCR).

FIG. 9 is a graph verifying a drug action mechanism by discovering a target of the montelukast using next-generation sequencing.

FIG. 10 is a graph A and a western blot result B illustrating an effect of protecting the inner ear tissue by causing the reduction of expression levels of a gene and a protein of Mmp3 by montelukast.

FIG. 11 is a diagram illustrating an effect of treating hearing loss when co-administrating montelukast and a *Ginkgo biloba* extract.

MODES OF THE INVENTION

Hereinafter, the present disclosure will be described in detail.

The present invention provides a composition capable of preventing or treating sensorineural hearing loss by preventing the damage of the inner ear organ sensing hearing to block the progression of a pathomechanism of the hearing loss, on the basis of an anti-inflammatory effect of montelukast which is a compound represented by the following Chemical Formula 1.

[Chemical Formula 1]

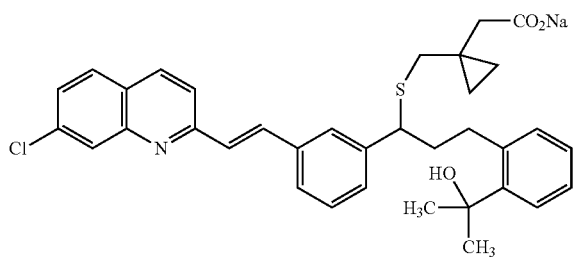

Further, the present invention provides a composition for preventing or treating sensorineural hearing loss using co-administration of the montelukast which is the compound represented by Chemical Formula 1 above and a *Ginkgo biloba* extract.

The composition is a concept including both of a pharmaceutical composition and a food composition.

The sensorineural hearing loss which can be treated or prevented by the compound represented by Chemical Formula 1 includes noise-induced hearing loss or presbycusis. The sensorineural hearing loss is caused by the damage of hair cells of the inner ear and the surrounding tissue thereof.

The compound represented by Chemical Formula 1 acts as an antagonist of a cysteinyl leukotriene receptor. The cysteinyl leukotriene receptor is expressed at the portion of a Corti's organ of the inner ear in a normal state.

As illustrated in FIG. 1 illustrating a pharmacological mechanism of the montelukast as the compound of the present invention, when the noise stimuli is provided to normal cochlea, the expression of the cysteinyl leukotriene receptor is increased at the Corti's organ, the blood vessels, and spiral ligament. Similarly, the expression of cysteinyl leukotriene as a fenofibrate is increased together as well as the receptor. In this situation, when alpha-q as one of subunits of a G protein is coupled with GTP by the cysteinyl leukotriene bound to the receptor to activate PLC, while PIP2 is converted to IP3, the secretion of calcium is promoted in an intracellular organelle to activate an apoptotic route, and as a result, the death of outer hair cells occurs. In this case, when the montelukast is treated, the activation of the G protein of the receptor does not occur and thus the activation of the apoptotic route is reduced.

The cysteinyl leukotriene receptor is a Type 1 receptor CysLT1. That is, the compound represented by Chemical Formula 1 is bound to the Type 1 receptor of the cysteinyl leukotriene to reduce the expression of a matrix metalloproteinase-3 (Mmp3) gene and thus has an effect of protecting hearing. Zinc-dependent endopeptidase made from the Mmp3 gene induces the degradation of an extracellular matrix associated with noise-induced hearing loss. The compound of Chemical Formula 1 reduces the expression even in a protein level (FIG. 10B) as well as a gene level (FIG. 10A).

Further, the pharmaceutical composition according to the present invention is for oral administration and administrated in a formulation selected from solid pharmaceutical preparations such as tablets, pills, capsules, powders, and granules, or oral liquid pharmaceutical preparations such as pharmaceutically acceptable aqueous solutions, suspensions, emulsions, syrups, pharmaceutical preparations which are dissolved in use, and elixirs.

The pharmaceutical composition is continuously administrated in the amount of 0.8 to 10 mg/kg for 4 to 14 days.

Further, the compound represented by Chemical Formula 1 may be co-administrated with a drug such as prednisolone, methylprednisolone, or a *Ginkgo biloba* extract. The prednisolone and the methylprednisolone are basically administrated in the amount of 5 mg and 4 mg twice a day, respectively and the doses thereof may be decreased or increased according to the judgment of a prescriber. The administrating period thereof is less than one month and required for preventing side effects of the drug such as a cushing's syndrome from occurring, and in the case of diabetic patients, a sudden change in blood sugar should be noted. The *Ginkgo biloba* may be co-administrated with the dose of 40 mg three times a day or 80 mg twice a day.

Further, when the composition is used as a food composition, the composition of the present invention is added in the amount of 15 wt % or less, and preferably, 10 wt % or less with respect to a raw material. However, in the case of long-term administration for health and hygiene or health control, the composition may be added in the amount of the above range or less. Since there is no problem in terms of safety, the active ingredient may be used in the amount of the above range or more.

The kind of food is not particularly limited. Examples of foods which may be added with the composition of the present invention include meat, sausages, bread, chocolate, candies, snacks, cookies, pizza, Ramen, other noodles, gums, dairy products including ice cream, various soups, beverages, tea, drinks, alcohol drinks, vitamin complex, and the like, and include all health foods in the accepted meaning.

When the food composition of the present invention is prepared as beverages, the composition of the present invention may include additional ingredients such as various flavorings and natural carbohydrates, like general beverages. The natural carbohydrates may be natural sweeteners such as monosaccharides such as glucose and fructose; disaccharides such as maltose and sucrose; dextrin and cyclodextrin, synthetic sweeteners such as saccharin and aspartame, or the like. The natural carbohydrates may be included in the amount of 0.01 to 10 wt %, and preferably, 0.01 to 0.1 wt % with respect to the total weight of the food composition of the present invention.

In addition, the food composition of the present invention may contain various nutrients, vitamins, electrolytes, flavoring agents, coloring agents, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like. Besides, the composition of the present invention may include pulps for preparing natural fruit juices, fruit juice beverages, and vegetable beverages. The components may be used independently or in combination. The ratios of the additives are not largely limited, but the additives may be included in the range of 0.01 to 0.1 wt % with respect to the total weight of the food composition of the present invention.

Anti-inflammatory drugs attempted for treatment of hearing loss in existing researches induce non-specific inflammatory response inhibition, but the present invention is characterized in that cysteinyl leukotrienes (CysLTs; LTC4, LTD4, and LTE4) and a cysteinyl leukotriene receptor type 1 (CysLT1 receptor) are specifically increased in hair cells of the hearing organ in a noise exposure environment to induce the anti-inflammatory action without side effects and inhibit the apoptosis of the hair cells (FIG. 1). Further, the present invention proposes posttreatment efficacy for inhibiting the progression of the hearing loss and reduces the expression of matrix metalloproteinase-3 which is one of zinc-dependent endopeptidases causing the degradation of the extracellular matrix, and thus, a normal function of a hearing system may be maintained by an effect of protecting an inner ear tissue.

Hearing-related diseases to be treated or prevented by the pharmaceutical composition to be provided by the present invention will be described in detail.

The "sensorineural hearing loss" occurs when components of the inner ear or accompanying nerve components is affected and may include nerve or sensing components when the auditory nerve of the brain or an auditory neural pathway is affected. The sensory hearing loss may be genetic or caused by acoustic trauma (for example, a very loud noise such as a blast explosion), viral infection, drug-induced or Meniere's disease. The neural hearing loss may be caused by brain tumors, infections, or various brain and nerve disorders, for example, stroke. Some genetic diseases, such as Refsum's disease (defective accumulation of branched fatty acids) may also cause neurological disorders affecting the hearing loss. The auditory neural pathway is damaged by a demyelinating disorder, for example an idiopathic inflammatory demyelinating disease (including multiple sclerosis), transverse myelitis, a devic's disease, progressive multifocal leukoencephalopathy, Guillain-Barre syndrome, chronic inflammatory demyelinating polyneuropathy, and anti-MAG peripheral neuropathy.

The "noise-induced hearing loss" occurs by the exposure to loud noises such as loud music and noise generated by heavy equipment or machinery, aircraft, artillery or other human for a long term. The hearing loss occurs by breakage of a hair cell receptor of the inner ear. The hearing loss is often accompanied by tinnitus. Often, permanent hearing damage is diagnosed. Currently, there is no method of treating the noise-induced hearing loss, but some treating methods including treatment using an insulin like growth factor 1 (IGF-1) are being developed. This refers to the document [Lee et al. Otol. Neurotol. (2007) 28: 976-981].

The "presbycusis" is age-related hearing loss, occurs as a part of normal aging, and occurs by degeneration of receptor cells in the Corti's spiral organ of the inner ear. Other causes may be due to flexibility loss of the basilar membrane of cochlea and reduction in the nerve fiber number of the vestibular cochlear nerve. The treating method for presbycusis or permanent hearing loss due to excessive noise is not currently known.

The present invention relates to a drug related with ear diseases and terms for structures of the ear will be described.

The "cochlea" is an inner ear part related with hearing. The cochlea is a spiral pipe-like structure would in the shape of resemble snail. The inside of the cochlea is divided into three regions and by a position of the vestibular membrane and the basilar membrane. A part above the vestibular membrane is the vestibular system and extended from the fenestra ovalis to the apex of the cochlea, and contains the perilymph which is aqueous liquid having the low potassium content and the high sodium content. The basilar membrane limits a scala tympani part and extended from the apex of the cochlea to the fenestra rotunda and contains the perilymph. The basilar membrane contains a lot of stiff fibers, and the length from the fenestra rotunda to the apex of the cochlea is gradually increased. The fiber of the basilar membrane is activated and vibrated by the sound. A cochlear duct is positioned between the vestibular system and the scala tympani and the end thereof is a sealed vesica in the apex of the cochlea. The cochlear duct contains an endolymph and the endolymph is similar to the cerebrospinal fluid and has the high potassium content.

The "Corti's organ" as the hearing organ is positioned on the basilar membrane and is extended upward to the cochlear duct. The Corti's organ contains hair cells having hair-like projections extended from the free surface and contacts the gelatin surface called a tectorial membrane. The hair cells has no neuraxis, but are surrounded by sensory nerve fibers forming cochlear branches of the vestibulocochlear nerve (brain nerve VIII).

As a detailed exemplary embodiment of the present invention, a process of verifying an effect of protecting a hearing organ by post-treatment of montelukast which is the compound of the present invention will be described.

In the present invention, as an implementation method, an already-established hearing loss animal model method is used, and it is advantageous that the method is very easily applied as hereafter clinical trials because the hearing systems in mammals including the human have the same anatomical histological structure. Further, it is advantageous that a hearing loss-induced time is short (a change in permanent hearing loss threshold after the lapse of two weeks of the damage to the hearing system) and an in vitro model system used for confirming existing pharmacological mechanisms can be used together. The montelukast concentration (10 mg/kg) used in the present invention is verified as a non-toxic level.

As illustrated in FIG. 2, in order to facilitate the description for experiments of the exemplary embodiments, experimental time was described in sequence. Noise stimuli were applied based on 0 day, montelukast was treated for 3 days, mice were sacrificed at 1 day, 3 day, 7 day, and 14 day, and then the changes thereof were observed. Immunohistochemistry, PCR, and a western blot test for examining changes in receptor expression levels by using tissues obtained at a noise stimulation test day, 1 day, 3 day, and 7 day were performed, respectively. Changes in permanent hearing threshold immediately before scarifying the mouse were verified by an auditory brainstem response test at 14 day and thereafter, a surface preparation method and a scanning electron microscopy test for evaluating the tissue damage were performed.

Example 1: Experiment for Verifying Whether Leukotriene Receptor is Present

It should be verified that a specific receptor by which the corresponding drug can act to a target organ is present so that the drug specifically acts. Cochlea of a normal 8-week-old male BALB/c mouse was extracted and whether the receptor is present at RNA gene levels was verified by using a polymerase chain reaction (PCR) method (FIG. 3A).

A detailed experimental method is as follows. At 1 day, 3 day, and 7 day, the animal was euthanized with urethane intraperitoneal injection (1 g/kg) and the bilateral temporal bone was immediately removed. Two isolated cochleae were dissolved in a TRIzol solution, the lipid was removed by adding chloroform, and then RNA gene was extracted with isopropanol alcohol. The extracted RNA gene was quantified, mixed with two types of forward and reverse primers and polymerase, and amplified at an average of 35 cycles for each primer through a PCR machine, and then changes in expression level for each gene were compared and analyzed by measuring the fluorescent degree. As a result, it was verified that as leukotriene receptor genes, endogenous mRNAs of CysLT1 (Cysltr1), CysLT2 (Cysltr2), and BLT1 (Ltb4r1) were expressed at the normal cochlea (FIG. 3A).

Example 2: Observation of CysLT1 Receptor and Change after Noise Exposure

In order to verify whether the CysLT1 receptors screened in Example 1 were increased by noise stimuli, an 8-week-old male BALB/c mouse was exposed using a noise generator for 3 hours in the sound pressure of 112 decibel. Thereafter, the cochlear tissue was extracted from the mouse and changes in expression level for each time were verified. Whether the receptors were present at RNA and protein levels, respectively, was verified by using a PCR method and a western blot (WB) method as a protein expression test method. In order to verify whether the non-specific increase is not present, different types of leukotriene receptors (CysLT2 receptor, BLT1 receptor, and BLT2 receptor) and LOX as a higher enzyme, and the like were verified by using the PCR. Changes in expression levels in the cochlea of the CysLTs (cysteinyl leukotrienes; LTC4, LTD4, and LTE4) by the increased LOX were verified by using an enzyme immunoassay (FIG. 3).

As a next step, an immunohistochemistry (IHC) to verify accurate action sites of the drug was used. An anatomical structure in which the corresponding receptor was expressed in the cochlea was verified by using a primary antibody for the CysLT1 receptor. Further, how the expression level of the receptor was changed during exposure of noise was compared and analyzed for each time and the result was used as a basic material for determining an appropriate drug administration period (FIG. 4).

A detailed experimental method is as follows (the PCR test refers to Example 1): At 1 day, 3 day, and 7 day, the animal was euthanized with urethane intraperitoneal injection (1 g/kg) and the bilateral temporal bone was immediately removed. In a western blot test, two isolated cochleae were homogenized in an ice-cold lysis buffer (100 mM Tris, pH 7.4, 200 mM NaCl, 1% NP-40, and 10 mM $MgCl_2$) which was added with a protease inhibitor. The western blot was performed according to an existing method. That is, a homogenate was centrifuged at 4° C. and 13,000 rpm for 20 minutes, proteins in a supernatant were electrophoresed by using 10% SDS-PAGE and transited to a nitrocellulose membrane. The membrane was incubated overnight with a primary antibody for a cysteinyl leukotriene receptor 1 (CysLT1; 1:1000 dilution; Caymen chemical, Ann Arbor, Mich.) and bands were determined by a chemiluminescence method (Ab Frontier, Seoul, Korea). The expression intensity of the bands was quantified by using ImageJ software (NIH, Bethesda, Md.).

An immunohistochemistry test method is as follows. The animal was anesthetized and perfused through the heart with a saline solution containing 0.5% sodium nitrate and heparin (10 U/ml). In addition, for tissue fixation, the animal was treated with 4% parafomaldehyde (PFA) dissolved in a 0.1 M phosphate buffer solution (pH 7.2). For obtaining the cochlea, temporal bones were dissected at both sides from the skull to be fixed overnight at 4° C. in 4% PFA. The fixed cochlea was washed three times with phosphate buffer saline (PBS) for 10 minutes and put in an ethylenediaminetetraacetic acid (EDTA) solution and the liminess was removed for 3 days. After decalcification, a sample was fixed with paraffin. Four sheets of continuous fragments with a thickness of 5 μm were obtained by using a sliding microtome (Leica, Wetzlar, Germany). The continuous fragments were placed on a gelatin-coated slide, rinsed with PBS three times, treated with 3% $H_2O_2$ for 5 minutes, and then rinsed with PBS (PBST) containing 0.2% Triton X-100. Non-specific binding was blocked by 1% bovine serum albumin (BSA) dissolved in the PBST. The fragments were incubated at 4° C. overnight together with the primary antibody for the cysteinyl leukotriene receptor 1 (CysLT1; 1:100 dilution;

Caymen chemical, Ann Arbor, Mich.). After rinsed with PBST, the fragments were incubated for 1 hour together with a biotinylated secondary antibody (Vector Laboratories, Burlingame, Calif.) and for 1 hour with an avidin/biotin system (Vector Laboratories) and colored by using 3,3'-diaminobenzidine (D5637, DAB, Sigma Aldrich) solution (0.05% DAB and 0.003% hydrogen peroxide in 0.1 M PB). Cell nuclei were contrast-dyed by using hematoxylin QS (H-3404, Vector Laboratories). An optical microscopic (light field) image was obtained by using PictureFrame Application 2.3 software.

As the experimental result, after the noise stimuli were applied, changes in expression level of the genes for each time were verified for 7 days (FIGS. 3B to 3E), and expression levels of the gene and the protein of only the Cysltr1 were significantly increased at 3 day after stimulation (FIGS. 3B and 3G). It was illustrated that 5-lipoxygenase (Alox5) on a higher pathway was similarly increased for each time (FIG. 3F), it was observed that the expression level of CysLTs as a fenofibrate of the CysLT1 receptor was also increased (FIG. 3H), and it was verified that a CysLT1 signaling system was activated under the noise stimuli. Further, as the immunohistochemical test result, it was verified the expression level of the CysLT1 receptor was significantly increased at 3 day after exposure of the noise at the spiral ligament (FIGS. 4G and 4H) and the corti organ (FIGS. 4G to 4I) as compared with a normal control group (FIGS. 4A to 4C) like the expression levels of the gene and the protein. As a result, in the following experiment, an antagonist of the cysteinyl leukotriene receptor was used.

Example 3: Measurement of Changes in Hearing Threshold

Whether the montelukast prevented noise-induced injury of the cochlea was evaluated (see FIGS. 5A and 5B). For evaluating and recording initial hearing before 1 day of exposure of noise, an auditory brainstem response (ABR) test as an electrophysiological test was performed (pre-ABR). ABR measurement was performed by the existing method, and hearing was evaluated by a Biosig 32 ABR system (Tucker-Davis Technologies, Gainesville, Fla.). Each mouse was anesthetized by intraperitoneal injection of chloral hydrate (Sigma Aldrich-Fluka, St. Louis, Mo.). A brainstem response was percutaneously recorded by using sterile electrode needle. A reference electrode was inserted behind the ear to be measured and active electrodes were inserted behind the opposite ear and the skin of the head. The stimuli were injected through an earphone which was directly positioned as an external hearing pathway. Until 16 or 32 kHz was automatically reduced up to 10 dB at 75 dB by 5 steps until ABF fluctuation disappeared by selecting a hearing frequency. At each frequency, averages of 1,000 stimuli were collected and respective results were recorded and stored. The hearing threshold was determined by the lowest intensity capable of extracting the fluctuation which was regenerable and visually detected. The ABR for 16 and 32 kHz stimuli was recorded before exposure of the noise and at 1 day and 14 day for exposure of the noise. That is, in order to evaluate acute hearing loss, changes in hearing threshold after 1 day of the exposure of the noise were measured (compound threshold shift; CTS). The changes in hearing threshold in a noise exposure group and a noise-exposure and montelukast-posttreatment group were compared and analyzed. In order to evaluate permanent hearing loss, changes in hearing threshold after 14 day of the exposure of the noise were measured (permanent threshold shift; PTS). The changes in hearing threshold in a noise exposure group and a noise-exposure and montelukast-posttreatment group were compared and analyzed (FIG. 5).

First, in order to verify efficacy of montelukast post-treatment, the changes in hearing threshold were calculated based on a difference between ABR thresholds before and after the noise exposure of each animal. A baseline ABR threshold (−1 day) has no significant difference between experimental groups. The compound threshold shift (CTS) after the noise exposure was measured at 1 day after the noise exposure and the permanent threshold shift (PTS) was measured at 14 day after the noise exposure. FIG. 5A illustrates that the compound threshold shift (CTS) had similar patterns at 16 and 32 kHz in both the only-noise exposure group and the montelukast post-treated group. On the other hand, when PTS was measured at 14 day of the noise exposure after the montelukast was administrated for 4 days, as compared with the only-noise exposure group, the threshold shift showed reduction of approximately 50% and an effect of protecting the hearing by the montelukast was verified (FIG. 5B).

Example 4: Verification of Effect of Protecting Hearing Hair Cells in Montelukast In a control group, an only-noise exposure group, a montelukast post-treatment group after noise exposure, after 1 week of the noise exposure, the inner ear tissue was extracted from the mouse and the sample was prepared by a surface preparation (SP) method.

In order to search the change of the hair cells, phalloidin staining was performed. The cut cochlea was perfused with 4% PFA in 0.1 M PB and maintained overnight at 4° C. The cochlea was washed with PBS three times for 10 minutes and then decalcified with a 5% EDTA solution for 3 days. After decalcification, an otic capsule was removed and a lateral wall, a Reissner's membrane, and a tectorial membrane were removed under an optical microscope. The Corti's organ (OC) was dyed with Texas Red VR-X phalloidin (T7471; 200 U/mL methanol diluted 1:100 in PBS; Invitrogen, Eugene, Oreg.) for 1 hour. Thereafter, the entire samples were rinsed with PBS and cut and placed on a glass slide by performing a surface treatment method (microdissected into individual turns) and using a mounting solution containing 4'6-diamidino-2-phenilindol (H-1200; 1.5 μg/ml; DAPI; Vector Laboratories). The slide was incubated for at least 15 minutes. The hair cells of the OC were observed by a confocal microscope (LSM510, Carl Zeiss, Jena, Germany). An examined region was a 32 kHz corresponding site above the hook region of the cochlea, and in a plurality of samples obtained from 4 mice for each experimental group, Texas-Red phalloidin as a hair cell component marker and a marker for a cell nucleus were observed by using a confocal microscopy and then it was compared and analyzed that the death of the hair cells was reduced by the montelukast (FIG. 6).

Through the surface preparation method, it was verified that in the noise exposure group, the hair cell marker was significantly decreased compared with the normal control group, but in the montelukast post-treatment group, the hair cell marker was significantly increased compared with the noise exposure group.

It was additionally verified by using a scanning electron microscopy (SEM) that apoptosis due to the noise exposure was reduced by the montelukast (FIG. 7). The SEM was used for evaluating the form of the hair cells of the cochlea. The mouse was euthanized after intraperitoneal injection of urethane, and temporal bones were dissected at both sides from the skull in order to obtain the cochlea to be carefully cut. The fenestra rotunda of the obtained cochlea was perforated by using a sharp needle. An outer lymph space was perfused with 2% glutaraldehyde in PBS by positioning a Pasteur pipette having a modified butterfly catheter for the fenestra rotunda. Each sample was left in a glutaraldehyde solution overnight. The samples were perfused with 1% osmium tetroxide and positioned at a tissue rotator for 15 minutes. The samples were rinsed with PBS three times. Under an optical microscope, the bone part of the cochlea was carefully removed and a lateral wall was cut and removed to expose the Corti's organ. The tissue was continuously dehydrated with 50, 70, 90, 95, and 100% acetones. Each specimen was treated with hexamethyldisilazane (HMDS) and dried in air, and positioned in a stove for coating of platinum. The tissue was photographed by JSM-6380 (Jeol, Tokyo, Japan). The damage to the hair cells was analyzed in basal turn areas corresponding to 32 kHz.

In the SEM image, in the only-noise exposed group, the large damage was shown at stereocilia of OHC compared with the control group and in the montelukast post-treatment group, the damage to the stereocilia of OHC was significantly reduced as compared with the only-noise exposed group (FIG. 7). Since the result coincides with the result of the surface treatment method, the montelukast post-treatment is to show that the death of the hair cells is efficiently decreased after excessive noise stimulus.

It was verified that the increase in the CysLT1 receptor by the noise exposure was decreased by the montelukast by the PCR method (FIG. 8). The PCR test method refers to Example 1.

As the Cysltr1 gene analysis result, the montelukast post-treatment illustrated a result that the CysLT1 receptor gene which had been increased in the noise exposure group was significantly decreased at 3 day after noise exposure and it was verified that the protection effect by the montelukast was caused in down regulation of the CysLT1 signaling system.

Example 5: Discovery of Drug Target Using Next-Generation Gene Analysis Method

At 72 hrs after noise exposure, the inner ear tissue of the mouse was extracted and targets applied with montelukast were discovered by an RNA-seq method as a next-generation gene analysis method, and thus hearing loss inhibition mechanisms of the drug were clearly analyzed (FIG. 9).

At 3 day after noise exposure, high-quality RNA gene samples (RQI>7) were obtained by using cochlear tissues obtained in the control group, a noise exposure group, and a montelukast post-treatment group and using Illumina® TruSeq™ RNA Sample Preparation Kit v2 (Illumina Inc. San Diego, Calif., U.S.) and then RNA containing poly-A was obtained by using magnetic beads attached with Poly-T oligo. RNA fragments cut at a high temperature were duplicated as complementary DNA by reverse transcriptase. The complementary DNA fragments were polymerized in the following condition by using Master Mix and Primer Cocktail included in a sample preparation kit (Illumina Inc.). 30 secs at 98° C.; 15 cycles, 10 secs at 98° C., 30 secs at 60° C., 30 secs at 72° C.; 5 mins at 72° C. PCR products were input in a flow cell channel at a concentration of 12 pM in a complementary cDNA library purified with Ampure XP beads and used for 2×100-bp paired-end sequencing on an illumina 2000 sequencing platform. Raw data was searched by using TopHat (v2.0.8). The RNA amount was compared and analyzed as fragments per kilobase of exon per million reads (FPKM) values by using Cuffdiff (Cufflinks v 0.8.3). The FPKM values were converted to log 2 and quantile-normalized for analysis.

As the next-generation gene sequencing result, at 3 day after noise exposure, when comparing the noise exposure group and the montelukast post-treatment group, a total of 13 genes were significantly changed. Particularly, Adam28, Reg3g, Mmp3, Ighv1-73, Snora16a, and Rp117-ps5 genes as inflammatory-related genes were increased in the noise exposure group, whereas had a similar expression level to the normal control group in the montelukast post-treatment group, and thus it was verified that the protection effect by the montelukast post-treatment was additionally achieved through down regulation of the genes (FIG. 9). Further, the montelukast post-treatment caused reduction of gene and protein expression levels of matrix metalloproteinase-3 (Mmp3) as zinc-dependent endopeptidase which caused degradation of the extracellular matrix in which association with noise-induced hearing loss was reported among the listed genes to have the effect of protecting the inner ear tissue (FIG. 10).

Example 6: Verification of Effect of Co-Administration of Montelukast and *Ginkgo biloba* Extract A hearing threshold shift effect according to treatment of montelukast and a *Ginkgo biloba* extract was verified. The experiment was performed in the same manner as Example 3. However, in the case of the montelukast, 10 mg/kg was used, and a *Ginkgo biloba* extract (EgB) (Tanamin Tab.) was orally administrated together with 32.4 mg/kg. The results were illustrated in FIG. 11.

As illustrated in FIG. 11, as compared with the only-noise treatment, the hearing protection effect was shown in only-montelukast administration, whereas in only-EgB administration, the effect was not shown. However, in co-administration of the montelukast and the *Ginkgo biloba* extract, a higher hearing protection effect was shown as compared with the only-montelukast treatment.

In this specification, exemplary embodiments of the present invention have been classified into the first, second and third exemplary embodiments and described for conciseness. However, respective steps or functions of an exemplary embodiment may be combined with those of another exemplary embodiment to implement still another exemplary embodiment of the present invention.

The invention claimed is:

1. A method of treating sensorineural hearing loss caused by damage to hair cells in an inner ear and surrounding tissue thereof, comprising administering to a subject in need thereof a therapeutically effective amount of a pharmaceutical composition comprising a compound of Chemical Formula 1:

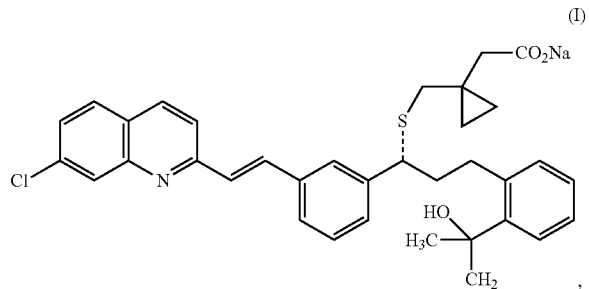

the pharmaceutical composition treating sensorineural hearing loss caused by damage to hair cells in an inner ear and surrounding tissue thereof in the subject.

2. The method of claim 1, wherein the sensorineural hearing loss is noise-induced hearing loss or presbycusis (age related).

3. The method of claim 1, wherein the pharmaceutical composition is administered orally.

4. The method of claim 1, wherein the pharmaceutical composition is co-administrated with at least one drug selected from prednisolone and methylprednisolone.

5. The method of claim 1, wherein the pharmaceutical composition is administered in amount of 0.8-10 mg/kg per day so as to downregulate a cysteinyl leukotriene receptor.

6. A method of improving sensorineural hearing loss caused by damage to hair cells in an inner ear and surrounding tissue thereof, comprising administering to a subject in need thereof an effective amount of a food composition comprising a compound of Chemical Formula 1:

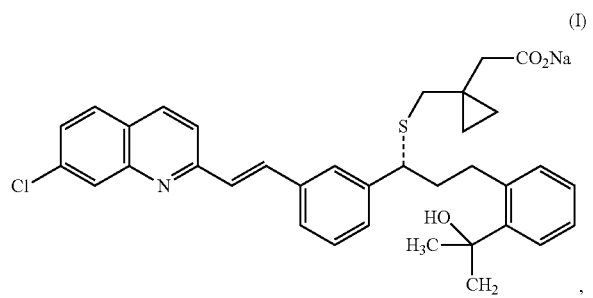

(I)

the food composition improving sensorineural hearing loss caused by damage to hair cells in an inner ear and surrounding tissue thereof in the subject.

7. A method of treating sensorineural hearing loss caused by damage to hair cells in an inner ear and surrounding tissue thereof, comprising administering to a subject in need thereof a therapeutically effective amount of a pharmaceutical composition comprising (a) a compound of Chemical Formula 1, and (b) a *Ginkgo biloba* extract:

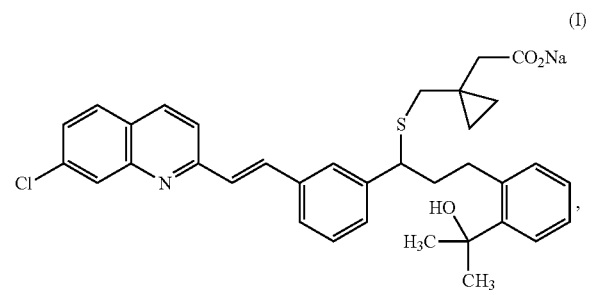

(I)

the pharmaceutical composition treating sensorineural hearing loss caused by damage to hair cells in an inner ear and surrounding tissue thereof in the subject.

8. The method of claim 7, wherein the sensorineural hearing loss is noise-induced hearing loss or presbycusis cage related).

9. The method of claim 7, wherein the compound of Chemical Formula 1 is an antagonist of and downregulates a cysteinyl leukotriene receptor.

10. The method of claim 9, wherein the cysteinyl leukotriene receptor is a cysteinyl leukotriene Type 1 receptor (CysLT1).

11. The method of claim 7, further comprising the pharmaceutical composition protecting the hair cells.

12. The method of claim 7, wherein the pharmaceutical composition is administrated orally.

13. The method of claim 12, wherein the pharmaceutical composition is administrated in a formulation selected from solid pharmaceutical preparations and oral liquid pharmaceutical preparations.

14. The method of claim 13, wherein the solid pharmaceutical preparations are selected from tablets, pills, capsules, powders, and granules.

15. The method of claim 13, wherein the oral liquid pharmaceutical preparations are selected from pharmaceutically acceptable aqueous solutions, suspensions, emulsions, syrups, pharmaceutical preparations which are dissolved in use, and elixirs.

16. The method of claim 7, wherein the compound of Chemical Formula 1 reduces the expression of a matrix metalloproteinase-3 (Mmp3) gene.

17. The method of claim 7, wherein the compound of Chemical Formula 1 reduces the level of zinc-dependent endopeptidase.

18. The method of claim 7, wherein the pharmaceutical composition is co-administrated with at least one drug selected from prednisolone and methylprednisolone.

19. The method of claim 7, wherein the pharmaceutical composition is administered in amount of 0.8-10 mg/kg per day so as to downregulate a cysteinyl leukotriene receptor.

20. A method of improving sensorineural hearing loss caused by damage to hair cells in an inner ear and surrounding tissue thereof, comprising administering to a subject in need thereof an effective amount of a food composition comprising (a) a compound of Chemical Formula 1, and (b) a *Ginkgo biloba* extract:

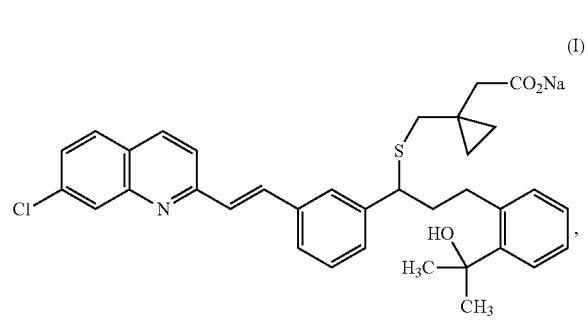

(I)

the food composition improving sensorineural hearing loss caused by damage to hair cells in an inner ear and surrounding tissue thereof in the subject.

* * * * *